US007869860B2

(12) United States Patent
Kinahan et al.

(10) Patent No.: US 7,869,860 B2
(45) Date of Patent: Jan. 11, 2011

(54) METHOD FOR ENHANCING THE ACCURACY OF PET/CT IMAGES

(75) Inventors: Paul E Kinahan, Seattle, WA (US); Adam M Alessio, Seattle, WA (US); Thomas K Lewellen, Port Ludlow, WA (US); Hubert J Vesselle, Mercer Island, WA (US)

(73) Assignee: University of Washington, Seattle, WA (US)

( * ) Notice: Subject to any disclaimer, the term of this patent is extended or adjusted under 35 U.S.C. 154(b) by 527 days.

(21) Appl. No.: 11/595,389

(22) Filed: Nov. 10, 2006

(65) Prior Publication Data
US 2007/0167716 A1   Jul. 19, 2007

Related U.S. Application Data (60) Provisional application No. 60/736,244, filed on Nov. 14, 2005.

(51) Int. Cl.
*A61B 5/05* (2006.01)
*G01N 23/04* (2006.01)
(52) U.S. Cl. ........................................ 600/425; 378/62
(58) Field of Classification Search .................. 600/425
See application file for complete search history.

(56) References Cited

U.S. PATENT DOCUMENTS

| | | | |
|---|---|---|---|
| 5,376,795 A | 12/1994 | Hasegawa | |
| 6,449,331 B1 | 9/2002 | Nutt | |
| 6,490,476 B1 | 12/2002 | Townsend | |
| 6,631,284 B2 | 10/2003 | Nutt | |
| 6,661,866 B1 | 12/2003 | Limkeman | |
| 6,754,298 B2 | 6/2004 | Fessler | |
| 6,885,762 B2 | 4/2005 | Saha | |
| 2003/0156684 A1 | 8/2003 | Fessler | |
| 2004/0030246 A1 | 2/2004 | Townsend | |
| 2004/0066909 A1 | 4/2004 | Lonn | |

(Continued)

OTHER PUBLICATIONS

Kinahan et al., PET/CT scanner instrumentation, challenges, and solutions, 2003, Elsevier Inc, vol. XXXIII, No. 3, pp. 166-179.*

(Continued)

*Primary Examiner*—Eric F Winakur
*Assistant Examiner*—Hien Nguyen
(74) *Attorney, Agent, or Firm*—Christensen O'Connor Johnson Kindness PLLC (57) ABSTRACT

A method is disclosed for obtaining linear attenuation coefficients for interpreting a PET scan of a region. The method is suitable for use when high molecular weight materials are present in the region, such as contrast agents or metal objects. The method includes obtaining first and second x-ray CT data sets of the region of interest at two different energies or voltage potentials and differencing corresponding CT numbers. The difference values are used to distinguish portions of the region that are bone from portions of the region that are contrast agent or other high molecular weight material. The obtained CT data set is then used to obtain an attenuation coefficient map of the region at the PET energy of 511 keV, for example, using a linear scaling factor suited to the particular identified material. Difference values at or near zero may be used to identify soft tissue portions of the region.

19 Claims, 6 Drawing Sheets

U.S. PATENT DOCUMENTS

2005/0129295 A1    6/2005    Shanmugam
2008/0226017 A1*  9/2008    Altman et al. .................. 378/4

OTHER PUBLICATIONS

Alessio, A.M., et al., "PET/CT Scanner Instrumentation, Challenges, and Solutions," Radiol. Clin. N. Am. 42:1017-1032, 2004.

Jackson, S., and R. Thomas (eds.), "Introduction to CT Physics," Cross-Sectional Imaging Made Easy, Churchill Livingstone, New York, Aug. 2004, pp. 3-16.

Kinahan, P.E., et al., "X-Ray-Based Attenuation Correction for Positron Emission Tomography/Computed Tomography Scanners," Seminars in Nuclear Medicine 33(3):166-179, Jul. 2003.

Trojan, A., et al., Fusion PET-CT Imaging of Neurolymphomatosis, Annals of Oncology 13(5):802-805, May 2002.

* cited by examiner

METHOD FOR ENHANCING THE ACCURACY OF PET/CT IMAGES

CROSS-REFERENCE TO RELATED APPLICATION

This application claims the benefit of Provisional Application No. 60/736,244, filed Nov. 14, 2005, the benefit of which is hereby claimed under 35 U.S.C. §119.

STATEMENT OF GOVERNMENT LICENSE RIGHTS

The U.S. Government has a paid-up license in this invention and the right in limited circumstances to require the patent owner to license others on reasonable terms as provided for by the terms of Contract No. CA-74135 awarded by the National Institutes of Health.

BACKGROUND

The present invention is in the field of medical imaging and, more particularly, to methods and systems relating to positron emission tomography.

Medical imaging technology has made remarkable advances in recent years, including developments and improvements in computed tomography ("CT"), magnetic resonance imaging ("MRI"), functional magnetic resonance imaging ("fMRI"), single photon emission computed tomography ("SPECT"), and positron emission tomography ("PET").

PET imaging has revolutionized imaging of internal biological regions by providing functional images of a patient or other region of interest. Positron emission tomography is a nuclear medicine medical imaging technique that produces a three-dimensional image or map of functional processes in the body, e.g., imaging that illuminates chemical and metabolic activity in the patient. The role of PET imaging in oncology research and patient care, in particular, is growing due to the ability of PET to add unique functional information to that obtained by conventional anatomical imaging modalities, for example CT.

PET scanning is an emissive technique wherein a short-lived radioactive tracer isotope, chemically combined with a metabolically active molecule such as a sugar, is injected into the subject. The metabolically active molecule becomes concentrated in the tissues of interest, concentrating the tracer isotope in regions of such activity. After injecting the isotope, the patient is placed on the scanner. As the injected isotope decays it emits a positron that annihilates with an electron, producing a pair of gamma rays or photons that travel in opposite directions. In general terms, the emitted photons are detected when they reach a scintillator material in the scanning device, creating a burst of light that is detected by photomultiplier tubes.

The detection technique relies on the coincident detection of the pair of photons to identify valid signals. Photons that are not detected within a few nanoseconds of each other are ignored. A straight line through the locations in the detector where the coincident photons are detected is called the line of response ("LOR"). The location of the positron emission is therefore known to lie somewhere along the LOR. The PET scanner uses the pair detection events and the LORs to map the density of the tracer isotope within the body. In a typical system, the images are generated along parallel slices separated by about 5 mm and the images are then combined to produce a three-dimensional image or model of the region of interest. The resulting map shows where the tracer isotope has become concentrated, identifying regions of metabolic activity in the body.

In most modern PET imaging systems, the PET scans are combined with CT scans, primarily to provide structural or anatomical information, to facilitate interpretation of the PET functional imaging. CT scans are a transmissive imaging technique wherein x-rays are transmitted through the region of interest and detected by detectors located generally opposite the x-ray source. The combination of PET scanning and CT scanning provides the medical professional with both anatomic and metabolic information for a patient. PET imaging is used heavily in clinical oncology (medical imaging of tumors and the search for metastases) and is also used in human brain and heart research.

The primary motivation in combining CT scanners and PET scanners is to obtain precise anatomical localization of regions identified on the PET tracer uptake images. A synergism with PET/CT scanners, however, is that the CT scanner data can be used to provide x-ray-based attenuation correction of the PET emission data, as discussed in more detail below.

Several physical effects can perturb tracer uptake images obtained with PET. The most significant of these effects are photon attenuation, scattered and random coincidences, detector efficiency variations, and scanner dead time. Of these, by far the most important is photon attenuation, which can affect both the visual quality and the quantitative accuracy of PET data. For example, in regions of non-uniform density, such as the thorax, the lack of attenuation correction can mask the appearance of solid lesions with moderately elevated tracer uptake.

The transmission of photons through any material can be characterized by a linear attenuation coefficient $\mu$. The linear attenuation coefficient depends on the photon energy E and the molecular weigh or atomic number Z of the material through which the photon passes. The linear attenuation coefficient can be defined as the probability per unit path length that the photon will interact with the absorbing material (for example, patient tissue). Photon attenuation includes two types of interactions—absorption and scatter. Linear attenuation coefficients for absorption are proportional to the density of the absorber and it is therefore common to express the attenuation property of a material in terms of its mass attenuation coefficient $\mu/\rho$, where $\rho$ is the density of the material. The total attenuation coefficient for an interaction is given by the sum of the possible photon interaction mechanisms, which for diagnostic imaging, are primarily photoelectric absorption and Compton scattering.

Figure 1:
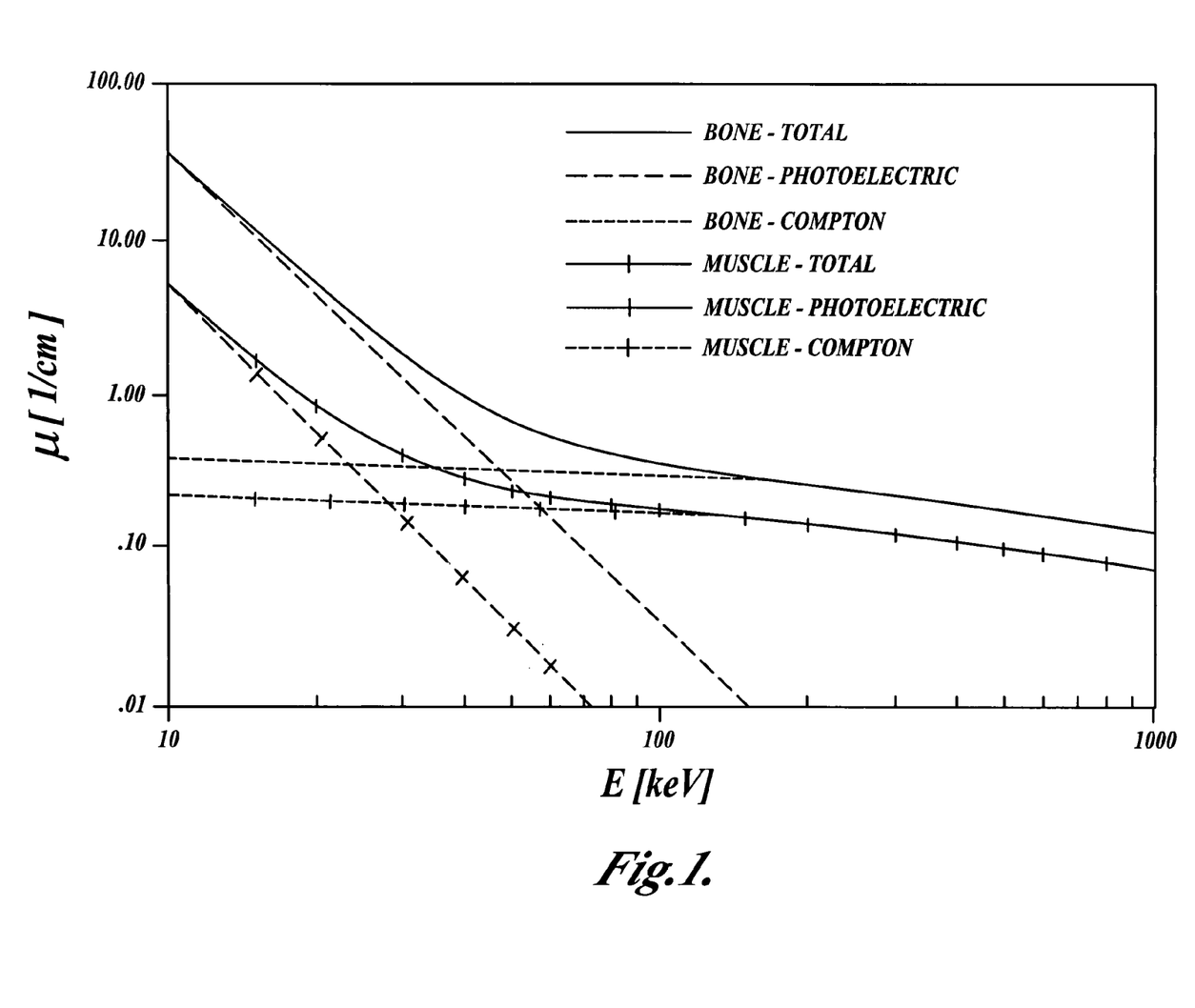
FIG. 1 shows the total attenuation coefficients as a function of photon energy for bone and for muscle, including the component of the attenuation coefficients due to photoelectric absorption and the components of the attenuation coefficients due to Compton scattering.

The total photoelectric and Compton linear attenuation coefficients for muscle and bone, as a function of photon energy in the range of 10 to 1,000 keV, are illustrated in FIG. 1. The portions of the total attenuation from photoelectric absorption and from Compton scattering are also shown. It can be seen from FIG. 1 that the total attenuation is dominated by photoelectric absorption below photon energies of about 30 keV for muscle and below about 50 keV for bone, and is dominated by Compton scattering for photon energies between about 200 keV and 1,000 keV.

The linear attenuation coefficient for Compton scattering is proportional to the atomic number of the material that the photon passes through. The mass attenuation coefficient for Compton scattering is, therefore, essentially independent of the material. For this reason, the mass attenuation coefficient for different materials converges for photon energies between about 200 keV to 1,000 keV where Compton scattering dominates. However, x-ray radiograph imaging generally utilizes the energy range from about 30 to 130 keV, where the total attenuation is sensitive to both photoelectric absorption and Compton scatter. PET imaging, in contrast, occurs at 511 keV, where photon attenuation by biological materials is determined primarily by Compton scattering.

It will also be appreciated that, for other compounds, including, for example, body-equivalent plastics or body regions represented by combinations of air and soft tissue (e.g., lungs) or combinations of soft tissue and bone, the mass attenuation coefficient can be calculated according to the mixture rule:

$$\frac{\mu}{\rho} = \sum_i \frac{w_i \mu_i}{\rho_i}$$

where $w_i$ is the proportion by weight of the i-th constituent. The mixture rule is accurate to within a few percent for photon energies above about 10 keV.

The physical process of photon attenuation obviously affects annihilation photons that are produced and detected in PET emission imaging. Attenuation correction factors generally must be derived from transmission data, such as CT scans, to correct the PET data for photon attenuation. If the object has a simple geometry and is homogeneous, then the attenuation correction factors for PET can be calculated assuming an a priori estimate of the object's geometry and knowledge of the materials and their attenuation coefficients in the object. This method avoids the need to acquire transmissive data, but in practice is only marginally useful in relatively simple situations. This approach introduces biases and will not work in heterogeneous anatomical regions such as the thorax. In these more complex regions, measured attenuation factors are needed.

The distribution of attenuation coefficients in the object can be measured by using transmission data—for example, using positron, γ-ray, or x-ray sources. Comparing transmission scans with and without the patient in the field of view allows a direct estimate of the attenuation along each line of response ("LOR").

With PET/CT scanners, a 511 keV attenuation map can be estimated from the CT image to correct the PET emission data for photon attenuation. There are four significant advantages of using CT to acquire transmission scans for attenuation correction of the PET emission data: First, the CT data has relatively low statistical noise as compared with transmission data acquired with radionuclide sources. Second, the CT scan data can be acquired much more quickly than a standard PET transmission scan. Third is the ability to collect uncontaminated post-injection transmission scans—an important practical consideration. Fourth, using x-ray transmission scanning eliminates the need for radionuclide transmission hardware and periodic replacement of the radionuclide sources. A potential benefit not yet fully explored is the direct incorporation of anatomical information derived from the CT data into the PET image reconstruction process.

However, as indicated in FIG. 1, the attenuation coefficient is also dependent on the energy of the photon. When used to correct PET emission data for photon attenuation, the data measured with x-ray CT must be converted to the appropriate attenuation coefficient values at 511 keV. Once the attenuation map at the correct energy is obtained, the attenuation correction factor for an individual sinogram element is calculated by numerically integrating the attenuation along the LOR corresponding to the emission sinogram element.

Although x-ray-based attenuation correction introduces very little noise, it has increased potential for introducing bias in the reconstructed emission images, particularly when the scanned region contains contrast agents or metal objects, as discussed in more detail below. To understand why x-ray-based attenuation correction can cause bias, we first consider the data obtained in CT imaging.

CT numbers are generally obtained in Hounsfield units (HU) and cannot be directly used to correct the emission data for photon attenuation at 511 keV. The Hounsfield scale is a quantitative scale for describing radiodensity. Radiodensity is the property of relative transparency to the passage of X-rays through a material.

If the material properties of the imaged region are known, then conversion between the CT numbers and the desired attenuation coefficients can be readily obtained. However, in heterogeneous regions the material properties may be difficult to determine. There are three general methods for converting the CT numbers to attenuation coefficients-segmentation, scaling, and dual-energy CT scans.

Segmentation methods separate the CT image into regions corresponding to different tissue types (for example, soft tissue, lung, bone) and the CT number for each tissue type is then replaced with an attenuation coefficient based on the tissue type at a photon energy of 511 keV. A significant problem with this method, however, is that some tissue regions have varying densities and may not be accurately represented by a single attenuation factor. In pulmonary regions, for example, the density of lung tissue varies by as much as thirty percent.

Scaling generally provides a more accurate estimate of the attenuation coefficient. In general, for a particular tissue type the image values produced by CT are approximately linearly related to the physical attenuation coefficient of that tissue type. It is therefore possible to estimate the attenuation map of the patient simply by multiplying the entire CT image by the ratio of attenuation coefficients of water (representing soft tissue) at the photon energies of CT and PET. However, different scaling factors are needed for bone (relatively high-Z) and soft tissue (relatively low-Z) to transform CT images acquired at x-ray energy values to calculate an attenuation map calibrated at the emission energy of 511 keV.

Figure 2:
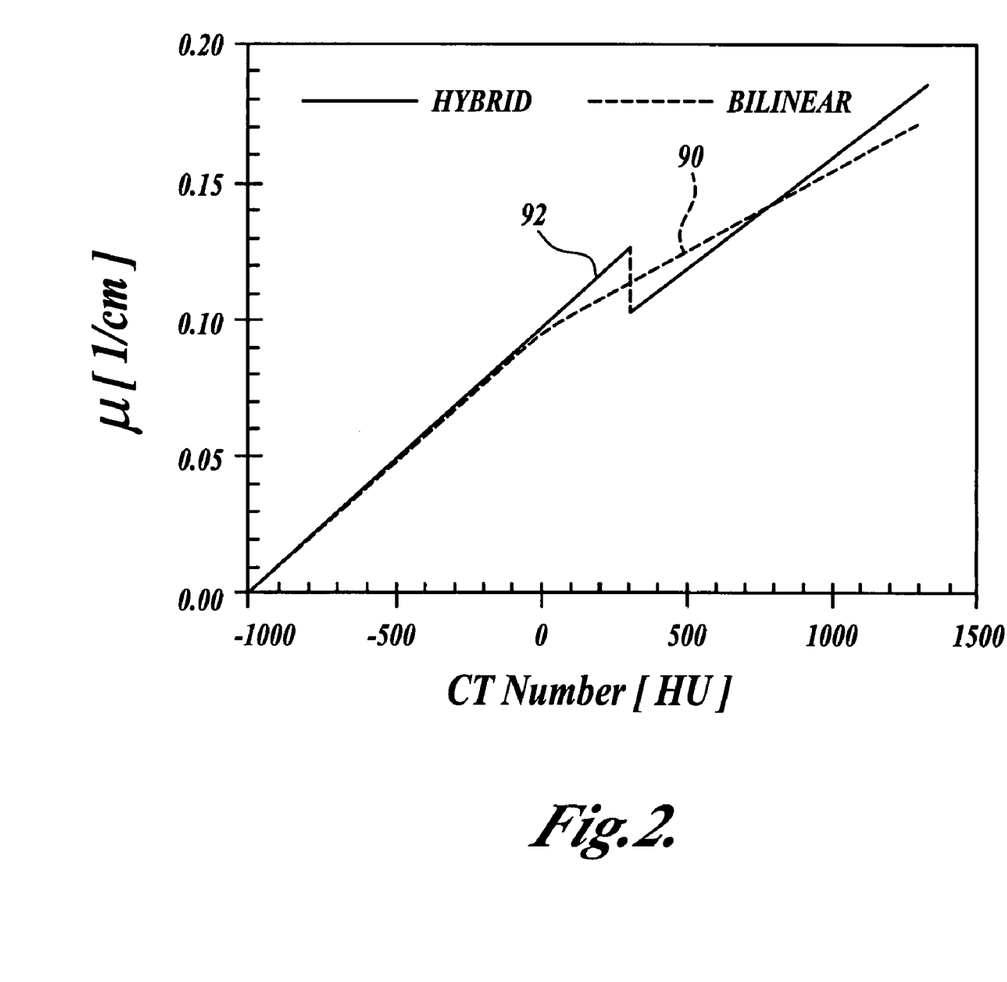
FIG. 2 illustrates an approximate conversion between the CT number and the linear attenuation coefficient for bilinear and hybrid methods based on a single CT image.

One approach to compensate for the high-Z materials is to note that CT numbers having a radiodensity in the range of −1,000<HU<0 primarily represents regions containing lung and soft tissues, whereas regions having CT numbers >0 primarily contain mixtures of soft-tissue and bone. Therefore, a bilinear scaling can be used to convert image CT numbers to attenuation coefficients—for example, as indicated by dashed curve 90 in FIG. 2, wherein the CT number is converted to an attenuation coefficient along a bilinear curve having one slope for a CT number less than 0 and a piecewise continuous portion with a different slope for a CT number greater than 0.

An alternative approach for converting CT images to attenuation maps is the so-called "hybrid method," which combines segmentation and scaling. Specifically, the attenuation map at 511 keV is estimated by first using a threshold CT number to approximately distinguish bone components in the CT image, and then using separate scaling factors for the mass attenuation coefficients of the bone and non-bone components. This hybrid method in converting CT numbers to linear attenuation coefficients is indicated by the piece-wise discontinuous curve 92 in FIG. 2, where the threshold for differentiating bone from non-bone regions was selected to be about 300 HU.

Although the hybrid method is not piece-wise continuous, unlike the bilinear method, there is no unique transformation from CT energies to 511 keV due to the possibility of independent variations in density and Z, which can cause two materials with similar CT numbers at some effective energy (say 70 keV) to have different attenuation coefficients at 511 keV. Conversely, it is possible for two distinct materials with the same value of attenuation coefficient at 511 keV to yield different CT numbers. Fortunately, both the bilinear scaling method and the hybrid method have been shown to give reasonable results for biological materials in practice. However, bias and other error can result when contrast agents or metal objects are present in the patient.

Dual energy x-ray imaging, in theory, provides an accurate solution to the problem of converting CT numbers to linear attenuation coefficients at 511 keV using a basis material decomposition approach. An exemplary state-of-the-art dual energy x-ray imaging method is disclosed in U.S. Pat. No. 6,754,298 to Fessler, which is hereby expressly incorporated by reference. This dual energy x-ray scanning disclosed by Fessler can be understood by regarding the attenuation coefficient as a weighted sum of photoelectric absorption and Compton scattering probabilities—in essence, a system with two components. If we were able to determine the attenuation due to the individual photoelectric and Compton components separately, they could be scaled separately to any energy and then added to obtain the total attenuation coefficient, as discussed above. A disadvantage of such an approach is that the dual-energy CT method calculates the attenuation map by forming a generalized subtraction of two separate CT scans in which the noise of the component CT scans adds in quadrature. Therefore, although existing dual-energy techniques potentially offer the highest degree of accuracy, they also can suffer from excessive noise.

For normal biological materials, the bilinear scaling method of x-ray-based attenuation correction for PET/CT scanners performs satisfactorily for clinical procedures. However, there is no unique transformation from CT energies to 511 keV when the examined region contains a complex mixture of material components having differing densities and molecular weights, such as tissue and CT contrast agents and/or metallic objects. A mismatch between the measured/calculated and true attenuation values can introduce biases and artifacts into the reconstructed PET image, particularly when contrast agent is present.

SUMMARY

A method is disclosed for estimating linear attenuation coefficients, for example for use in interpreting positron emission tomography data, that is particularly suitable for medical imaging of regions of a body containing relatively high molecular weight material such as contrast agent, metals or the like. In a preferred embodiment of the invention, a relatively low-energy x-ray image of the region is obtained to generate a first data set of radiodensity values, e.g., in HU. A second x-ray scan of the region is taken at a relatively high-energy to generate a second data set of radiodensity values. The difference between the radiodensity values at corresponding locations in the data sets (i.e., at voxels corresponding to the same physical location in the imaged region) are then calculated, and the calculated differences are used to identify locations containing the relatively high molecular weight material and regions containing relatively low-molecular weight material, such as bone. Linear attenuation coefficients at the desired energy level, for example at 511 keV for PET imaging, are then calculated using different correlations for the high- and low-molecular weight materials.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

As discussed in detail above, quantitative mismatches can arise from the incorrect conversion of radiodensity measurements-for example, CT numbers obtained in conventional CT scanning-to linear attenuation coefficients at 511 keV. The presence of contrast agent(s) in the patient during the CT scan can cause significant errors in the 511 keV attenuation map when using the bilinear or hybrid conversion methods. In cancer imaging, for example, iodinated intravenous contrast agents are necessary for detection of lesions in solid organs and to better identify lymph nodes. As another example, oral contrast agent is typically administered to differentiate normal from abnormal bowel and to differentiate bowel from mesenteric masses. Concurrent intravenous and oral contrast enhancement is therefore critical for cancer staging with CT scanning and often is necessary for correlation with FDG (fluorodeoxyglucose) PET staging studies.

Intravenous contrast agents generally have iodine concentrations of 300 to 380 mg/mL. Oral contrast agents are usually based on barium. Contrast agents have a high atomic number (53 for iodine and 56 for barium) and radiodensity, which results in a high mass attenuation coefficient at x-ray photon energies because of photoelectric absorption. In the absence of intravenous contrast, vascularized tissues have CT numbers, or radiodensity, in the range of 30 to 60 HU. Immediately after a bolus injection of iodinated contrast media, the CT numbers can reach up to 200 to 300 HU for the aorta or the renal cortex. However, at 511 keV, the mass attenuation coefficient of iodine and barium is essentially the same as water or tissue. The values of contrast-enhanced CT numbers range from 0 to 300 HU, although the true linear attenuation coefficient at 511 keV for iodine varies little. Thus any scale factor that correctly predicts the attenuation coefficient at 511 keV for bone or soft tissue will overestimate the attenuation at 511 keV for contrast agent and vice-versa.

Focal accumulation of contrast agent—for example, in an artery during a bolus injection—can result in artifactual hot spots in the PET emission image in the same location. An accumulation of contrast agent, however, does not significantly affect PET emission images that are not attenuation corrected. Even at lower concentrations, with the overlap in CT numbers for contrast-enhanced and non-enhanced tissues, it is difficult to decide on the true attenuation coefficient based solely on the CT number.

As a first approach to CT-based attenuation correction ("CTAC") in PET imaging the scaling method discussed above and illustrated in FIG. 2, was developed. An improved scaling method is disclosed herein that provides a robust method that is particularly suitable when contrast agent is present in the scanned region. The method enables the clinician to distinguish bone from contrast agent, even when the CT numbers for the bone and contrast agent overlap in a particular CT scan.

Figure 3:
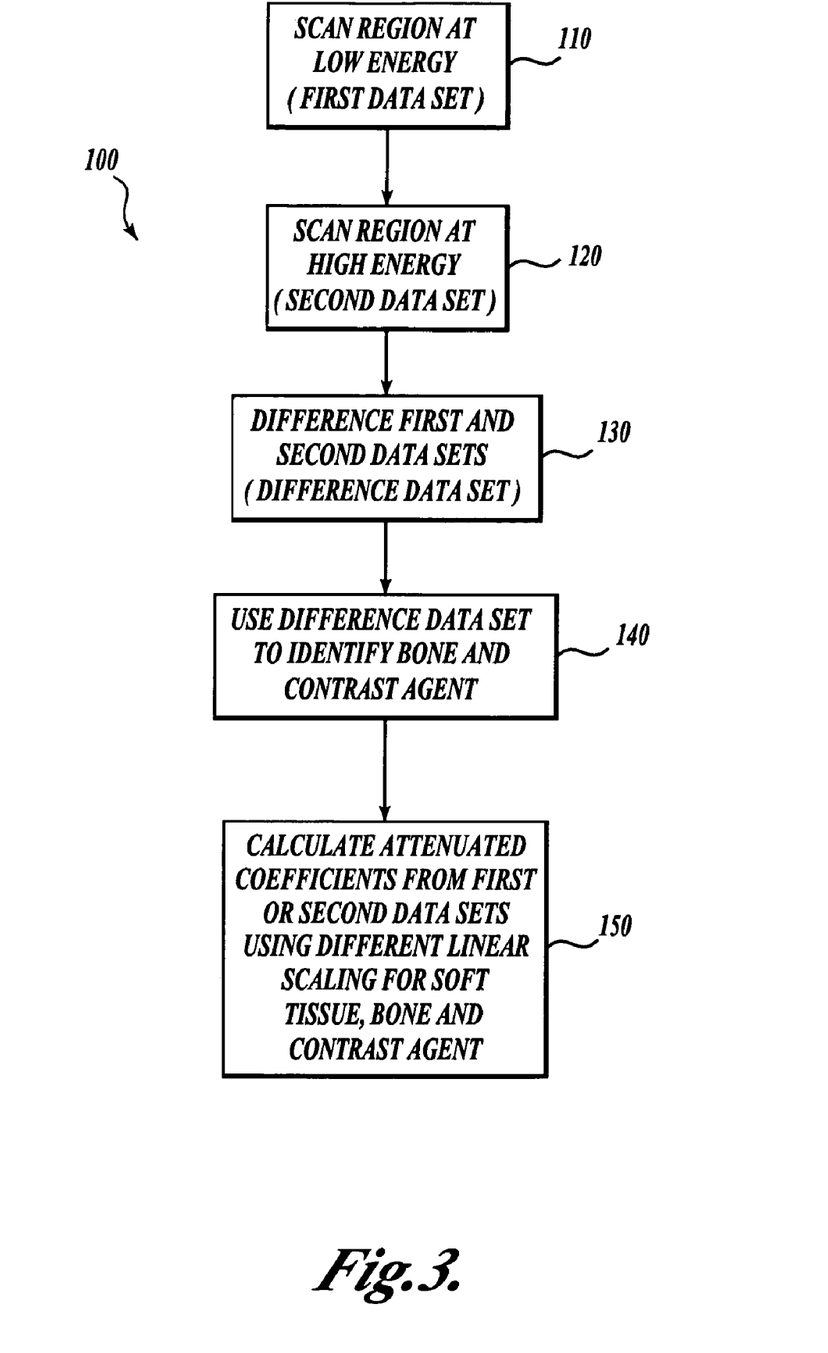
FIG. 3 is a block diagram illustrating a new scaling method for calculating attenuation coefficients utilizing two CT scan data sets obtained at different energies.

Refer now to FIG. 3, illustrating a block diagram providing an overview of a method 100 for calculating attenuation factors. In this embodiment, a CT scan of a region of a patient or object is taken at a relatively low energy level or voltage potential—for example, 80 kVp—to generate a first CT data set 110.

It will be appreciated by the artisan that in an x-ray generator the high-voltage potential between the cathode and the anode affects the speed at which electrons travel and strike the anode. The higher the kilovoltage potential (kVp), the more speed and, therefore, energy the electrons have when they strike the anode. Electrons striking with more energy results in X-ray with more penetrating power. The high-voltage potential is measured in kilovolts, and this is typically controlled with a voltage or kilovoltage control on a control console. An increase in the kilovoltage will also result in an increase in the peak energy of the radiation, which is distributed over a continuous spectrum or range.

Typically, the CT image data set comprises a three-dimensional set of CT numbers corresponding to each voxel in the data set. A second CT scan of the region is taken at a different kVp setting to generate a second three-dimensional CT data set 120. Corresponding points in the first and second CT data sets 110, 120 are differenced to generate a CT difference data set 130. The CT difference data set 130, relative to the values in the first (or second) CT image (e.g., FIG. 6), is used to identify portions of the first or second CT data sets corresponding to locations in the scanned region that are primarily bone and to similarly identify portions of the CT data sets corresponding to locations in the scanned region that are primarily contrast agent 140. Different scaling conversions may then be used to convert the CT numbers in the first CT data set and/or second CT data set from HU to attenuation coefficients at 511 keV.

In one embodiment of the present invention, the difference data set is also used to identify locations in the scanned region corresponding to water/air/soft tissue, such regions having a difference value that is usually substantially equal to or near zero. Alternatively, water/air/soft tissue may be identified from one of the CT data sets (preferably the higher kVp data set) as regions wherein the CT number is less than or equal to zero (or another appropriate threshold value, as discussed above).

Having identified for each relevant voxel in the difference data set the primary composition of the corresponding location in the scanned region, each corresponding voxel in either (or both) of the two CT data sets can now be converted from the CT number to an appropriate linear attenuation coefficient at 511 keV, using known or readily obtainable conversions. That is, the value in each voxel in the selected CT data set is converted to an attenuation coefficient based on the scanned CT number, and the determined composition.

Figure 4A:
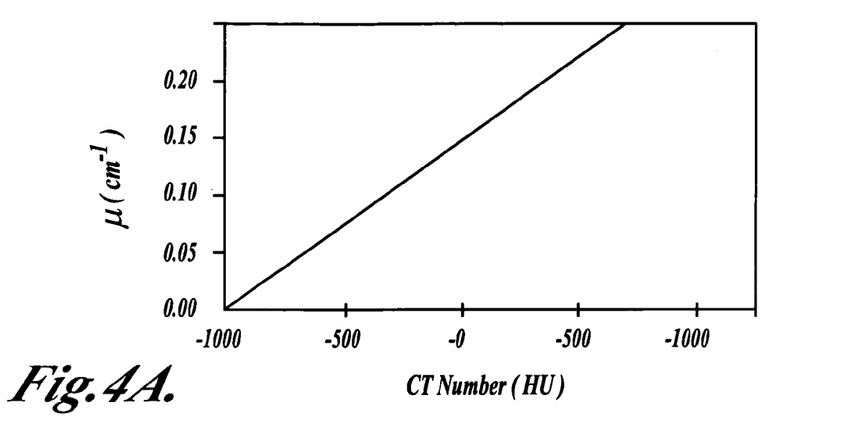
FIGS. 4A, 4B, and 4C show illustrative linear conversion curves for converting between CT numbers and linear attenuation curves for soft tissue, contrast agent, and bone, respectively.
Figure 4B:
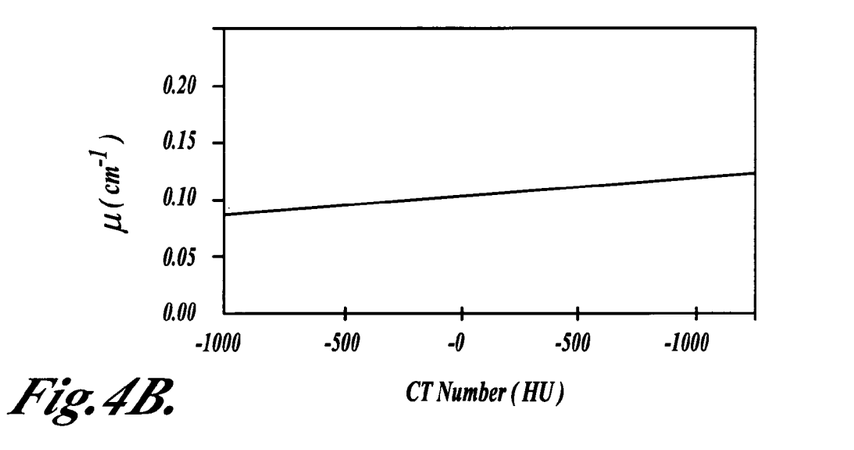
Figure 4C:
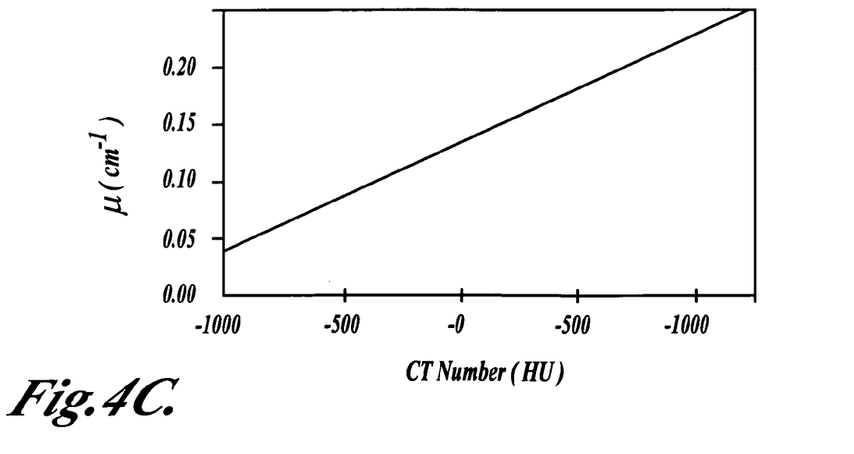

For example, FIGS. 4A-4C show three illustrative curves for converting CT numbers to linear attenuation coefficients at 511 keV. FIG. 4A shows a curve for converting CT numbers obtained for soft tissue, water, and air; FIG. 4B shows a curve for converting CT numbers obtained for contrast agent; and FIG. 4C shows a curve for converting values obtained for bone.

This method extends the scaling method described in the background section above to distinguish voxels having values for locations that are dominated by contrast agent from voxels having values for locations dominated primarily by bone. The calculated attenuation coefficients are then used to interpret the PET data for the region in a conventional manner as is well known in the art. This scaling method utilizes two different-energy CT data sets and takes advantage of the large differences in the photoelectric cross sections of the contrast agent as compared with calcium or bone, to determine how to scale each voxel in the CTAC image.

Figure 5:
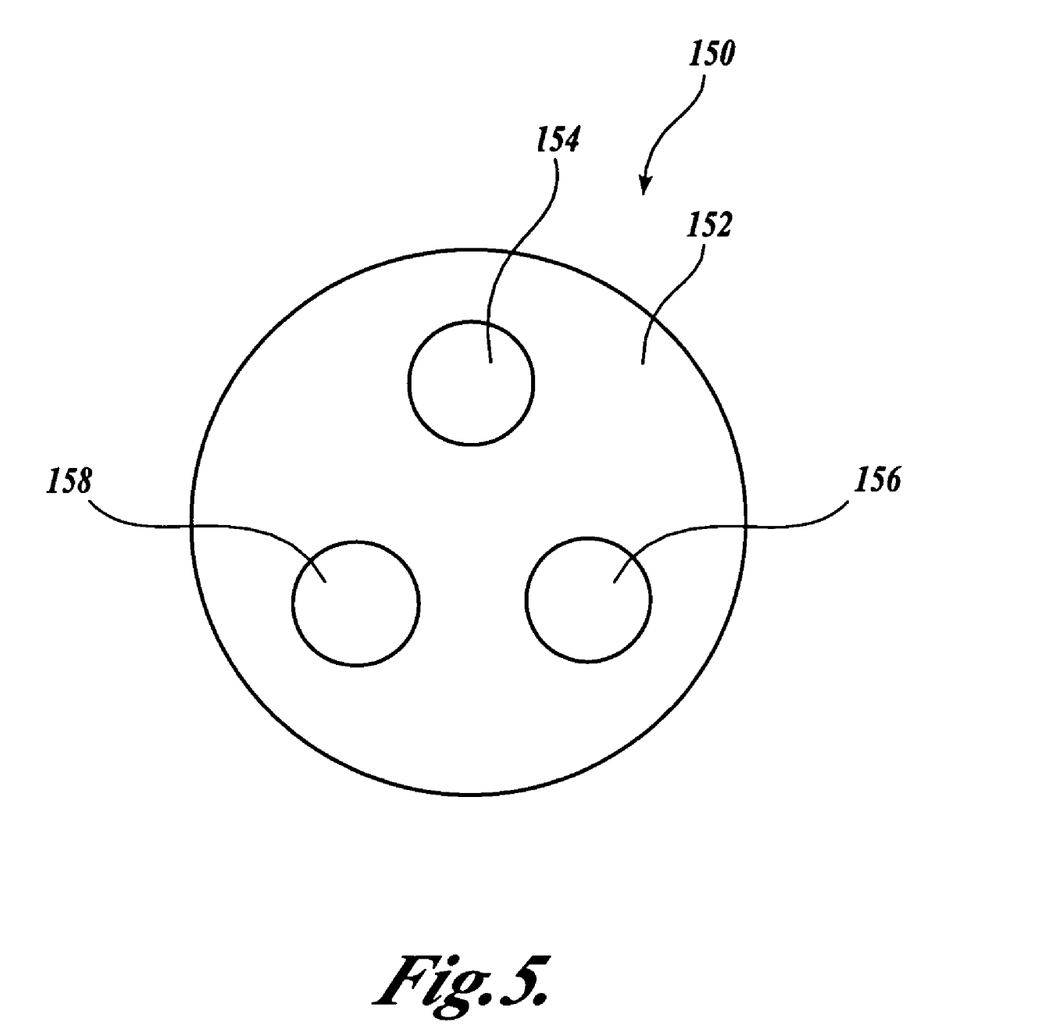
FIG. 5 shows a cross section of a two-dimensional test phantom used to validate a method in accordance with the present invention.

FIG. 5 is a sketch of a cross section of a 20 cm diameter test phantom 150 that was used as a test model to acquire CT number measurements at 80, 100, 120, and 140 kVp. The test phantom 150 is a tube containing water 152, a 5 cm-diameter cylinder containing air 154, a 5 cm-diameter cylinder containing dilute iodine-based contrast agent 156, and a 5 cm-diameter cylinder containing $CaCl_2$ in solution 158 (simulating bone equivalent atomic number). The resulting CT numbers (from a conventional clinical reconstruction) were evaluated at each tube voltage.

For example, when the CT numbers corresponding to the air and water were differenced between the values obtained from a scan at 80 kVp and a scan obtained at 140 kVp, there was essentially no variation in CT number for air 154 or water 152 with tube voltage. As noted above, this aspect permits identification of the air/water/soft tissue solely from the difference between two data sets.

For the $CaCl_2$ solution 158 simulating bone, however, the CT numbers increased by about 278 HU as the tube voltage was dropped from 140 to 80 kVp. The contrast agent 156 CT numbers increased by about 700 HU as the tube voltage was dropped from 140 to 80 kVp.

Therefore, when the CT number data set obtained from the 140 kVp scan is differenced from the CT number data set obtained from the 80 kVp scan, the resulting difference data set was essentially zero for the air 154 and water 152, but contained significantly different values for the $CaCl_2$ 158 and contrast agent 156. In particular, the difference data set values for contrast agent differed from the difference data set values for $CaCl_2$ by more than 400 HU.

Figure 6:
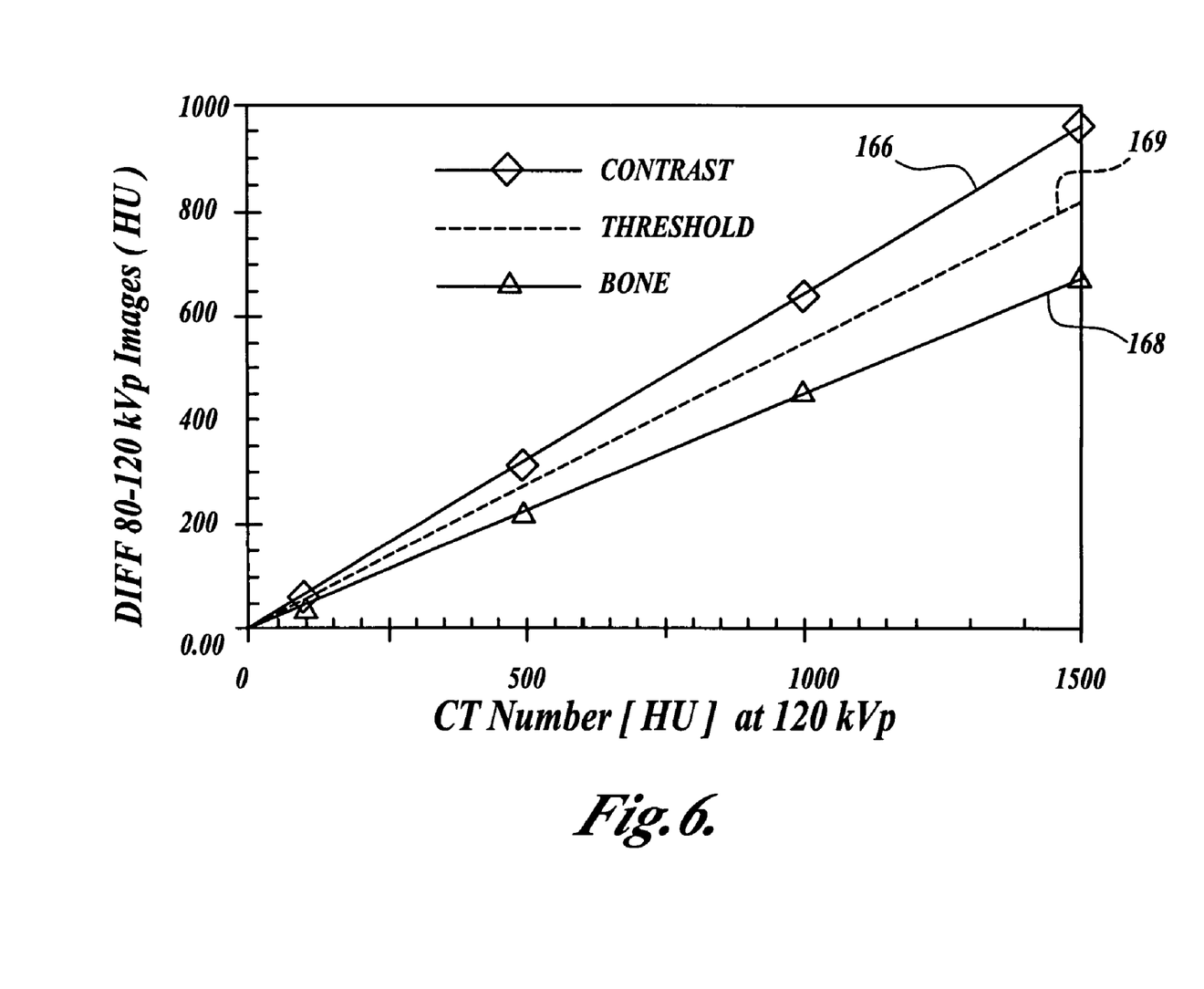
FIG. 6 illustrates the measured CT numbers plotted against the corresponding CT difference values, i.e., the CT number measured for the 80 kVp scan minus the CT number measured for the 120 kVp scan.

Based on these results, a classification scheme for difference data sets was derived using a midpoint of the relative change in CT numbers. The difference data set values were plotted against the CT numbers from one of the CT scans, and were found to increase approximately linearly with the CT numbers, wherein the CT number values account for variable concentrations of contrast agent and variable bone density, as indicated in FIG. 6. FIG. 6 shows the measured CT numbers plotted against the corresponding CT difference values, e.g., the CT number measured for the 80 kVp scan minus the CT number measured for the 120 kVp scan. The corresponding curve for the contrast agent 166 is generally steeper than the curve for the bone equivalent (CaCl$_2$) 168. The currently preferred classification scheme uses the midpoint between these curves 166 and 168 shown as a dashed line 169 in FIG. 6 as a threshold, so that voxels having a difference above the dashed line 169 are classified and scaled as contrast agents (e.g., from FIG. 4B), whereas voxels having a difference below the dashed line 169 are classified and scaled as bone (e.g., from FIG. 4C).

For example, in FIG. 6, the threshold dashed line 169 may be characterized by the equation Diff=0.53*CTN, where Diff is the difference between the CT numbers at 120 kVp from the corresponding CT numbers at 80 kVp, and CTN is the CT number at 120 kVp. To identify voxels corresponding to contrast agent, therefore, if Diff is greater than (0.53*CTN) for a voxel, then it corresponds to contrast agent and an appropriate conversion of the corresponding CT number to an attenuation coefficient at 511 keV can be made. If Diff is less than (0.53*CTN) and the voxel does not correspond to soft tissue (e.g., near zero value), then it corresponds to bone and an appropriate conversion of the CT number to attenuation coefficient can be made.

It will be appreciated that zero-value voxels in the difference data set correspond to air and water. Therefore, in a variation on the present method, the classification voxels corresponding to air and water may be based on a minimum value for the difference data, rather than relying on the raw data in one or both of the CT data sets.

This hybrid/bilinear scaling method was tested with measured CT and PET transmission data to evaluate the effect of increased statistical noise with 100 times fewer photons on classification errors and impact of statistical reconstruction methods. In this revised testing, we have found that with this dual-energy hybrid method it is possible to discriminate contrast versus bone in the CT attenuation correction images and apply the correct scale factor for accurate calibration and attenuation correction even at very low exposure levels for the second CT scan.

Although the method described is suitable for calculating suitable attenuation factors in regions having a single high-Z material, such as a contrast agent present, it is contemplated that the method may be readily extended to include more than two CT scans at different energies to discriminate between multiple high-Z materials present in a particular application.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for estimating linear attenuation coefficients at a particular photon energy for a three-dimensional region of a body comprising the steps of:
    scanning the three-dimensional region with an x-ray beam at a first kVp setting to generate a first CT image data set of values that indicate radiodensity at points in the three-dimensional region;
    scanning the three-dimensional region with an x-ray beam at a different kVp setting to generate a second CT image data set of values that indicate radiodensity at points in the three-dimensional region;
    calculating the differences in corresponding values in the first and second CT image data sets wherein the differences are calculated between points in the first and second CT image data sets that correspond to the same physical location in the three-dimensional region;
    estimating from the calculated differences portions of the three-dimensional region that are relatively low molecular weight material;
    estimating from the calculated differences portions of the three-dimensional region that are relatively high molecular weight material; and
    estimating linear attenuation coefficients for the three-dimensional region using one of the first and second CT image data sets and a first conversion factor for the relatively low molecular weight material and a second conversion factor for the relatively high molecular weight material, wherein the first conversion factor is different from the second conversion factor.

2. The method of claim 1, wherein the relatively low molecular weight material is bone.

3. The method of claim 1, wherein the relatively high molecular weight material is a contrast agent.

4. The method of claim 3, wherein the contrast agent is a solution containing one of barium and iodine.

5. The method of claim 1, wherein the first x-ray scan is taken at a tube voltage potential of between about 80 kVp and 100 kVp, inclusive.

6. The method of claim 1, wherein the second x-ray scan is taken at a tube voltage potential of between about 120 kVp and 140 kVp, inclusive.

7. The method of claim 1, wherein the attenuation coefficients are estimated for a photon energy of 511 keV.

8. The method of claim 1, further comprising estimating a difference threshold as a function of radiodensity, wherein the calculated differences above the threshold value are identified as relatively high molecular weight material.

9. The method of claim 8, wherein the difference threshold is a linear function of radiodensity.

10. The method of claim 1, further comprising using one of the first and second CT image data sets to identify portions of the three dimensional region that are a soft tissue.

11. A method for calculating linear attenuation coefficients in a three-dimensional region of a body comprising the steps of:
    using x-ray computed tomography at a first kVp setting to generate a first CT image data set containing radiodensity values of the three-dimensional region;
    using x-ray computed tomography at a different kVp setting to generate a second CT image data set containing radiodensity values of the three-dimensional region;
    computing the difference between corresponding radiodensity values in the first and second CT image data sets wherein the differences are calculated between points in the first and second data sets that correspond to the same physical location in the three-dimensional region;
    determining from values obtained in differencing the first and second data sets locations in the three-dimensional region corresponding to bone;
    determining from values obtained in differencing the first and second data sets locations in the three-dimensional region corresponding to contrast agent;
    estimating linear attenuation coefficients for locations in the region corresponding to bone based on a first curve correlating radiodensity values with linear attenuation coefficients for bone; and
    estimating linear attenuation coefficients for locations in the three-dimensional region corresponding to contrast agent based on a second curve correlating radiodensity values with linear attenuation coefficients for contrast agent.

12. The method of claim 11, wherein the contrast agent is a solution containing one of barium and iodine.

13. The method of claim 11, wherein the first kVp setting x-ray computed tomography uses a tube voltage potential of between about 80 kVp and 100 kVp, inclusive.

14. The method of claim 11, wherein the second kVp setting x-ray computed tomography uses a tube voltage potential of between about 120 kVp and 140 kVp, inclusive.

15. The method of claim 11, wherein the attenuation coefficients are estimated for a photon energy of 511 keV.

16. The method of claim 11, further comprising estimating a difference threshold as a function of radiodensity, wherein the calculated differences above the threshold value are identified as contrast agent.

17. The method of claim 16, wherein the difference threshold is a linear function of radiodensity.

18. The method of claim 11, further comprising using one of the first and second data sets to locations in the three-dimensional region that are a soft tissue.

19. The method of claim 11, wherein the calculated linear attenuation coefficients are estimated as linear functions of the measured radiodensity values.

* * * * *